US012121245B2

(12) United States Patent
Hafez et al.

(10) Patent No.: US 12,121,245 B2
(45) Date of Patent: Oct. 22, 2024

(54) PATIENT-SPECIFIC TEMPLATES FOR PEDICAL SCREW INSERTION IN CORRECTIVE SCOLIOSIS SURGERIES

(71) Applicants:Mahmoud Alm El Din Hafez, Giza (EG); Abdullah Ahmed Al Othman, Alkhober (SA)

(72) Inventors: Mahmoud Alm El Din Hafez, Giza (EG); Abdullah Ahmed Al Othman, Alkhober (SA)

(73) Assignee: Mahmoud Alm El Din Hafez, Giza (EG)

( * ) Notice: Subject to any disclaimer, the term of this patent is extended or adjusted under 35 U.S.C. 154(b) by 1023 days.

(21) Appl. No.: 16/647,576

(22) PCT Filed: Sep. 12, 2018

(86) PCT No.: PCT/EG2018/000014
§ 371 (c)(1),
(2) Date: Mar. 16, 2020

(87) PCT Pub. No.: WO2019/052623
PCT Pub. Date: Mar. 21, 2019

(65) Prior Publication Data
US 2020/0229856 A1 Jul. 23, 2020

(30) Foreign Application Priority Data

Sep. 14, 2017 (EG) ................................ 2017090025
Mar. 13, 2018 (EG) ................................ 2018030448

(51) Int. Cl.
*A61B 17/17* (2006.01)
*A61B 17/88* (2006.01)
*A61B 17/56* (2006.01)

(52) U.S. Cl.
CPC ...... *A61B 17/1757* (2013.01); *A61B 17/8897* (2013.01); *A61B 2017/568* (2013.01)

(58) Field of Classification Search
CPC . A61B 17/88; A61B 17/8897; A61B 17/8872; A61B 17/90; A61B 17/1757; A61B 2017/568
See application file for complete search history.

(56) References Cited

U.S. PATENT DOCUMENTS

D672,038 S * 12/2012 Frey ................... A61B 17/1757
D24/140
D705,929 S * 5/2014 Frey ................... A61B 17/1757
D24/140

(Continued)

FOREIGN PATENT DOCUMENTS

WO 2016075581 5/2016

OTHER PUBLICATIONS

International Search Report of PCT/EG2018/000014, Mailed on Feb. 21, 2019.

*Primary Examiner* — Julianna N Harvey
(74) *Attorney, Agent, or Firm* — Dickinson Wright PLLC; Andrew D. Dorisio

(57) ABSTRACT

This invention relates to a surgical device for the detection of the pedicle screws trajectories of a patient undergoing to scoliosis or spondylosis correction. The device is a patient specific and has information about screw size and position. The increased use of pedicle screws in scoliosis creates a challenge for accurate and safe placement of screw within the pedicle during the scoliosis surgery. Patient-specific templates (PST), is an alternative method to guide the surgeons for detecting the positions and trajectories of pedicle screws in scoliosis and spondylosis fixation surgery. This 3D model constructed during PST process can be also 3D printed as a physical model, which can help surgeons to (Continued)

develop an accurate and safe position of pedicle screws and its trajectories. This device has the ability to customize the placement and the size of each pedicle screw based on the unique morphology and landmarks of the vertebrae.

20 Claims, 9 Drawing Sheets

(56) References Cited

U.S. PATENT DOCUMENTS

| | | | |
|---|---|---|---|
| 2009/0024132 A1* | 1/2009 | Blain | A61B 17/1728 606/96 |
| 2009/0312764 A1* | 12/2009 | Marino | A61F 2/4455 606/86 R |
| 2012/0245587 A1* | 9/2012 | Fang | A61B 17/1671 606/80 |
| 2013/0145812 A1* | 6/2013 | Kawaguchi | B21F 1/00 140/123 |
| 2013/0218163 A1* | 8/2013 | Frey | A61B 17/1671 606/86 R |
| 2014/0350614 A1* | 11/2014 | Frey | A61B 34/10 606/86 R |
| 2017/0311961 A1* | 11/2017 | Lipari | A61B 17/1757 |
| 2019/0105065 A1* | 4/2019 | Sharifi-Mehr | A61B 17/1604 |

* cited by examiner (10)

PATIENT-SPECIFIC TEMPLATES FOR PEDICAL SCREW INSERTION IN CORRECTIVE SCOLIOSIS SURGERIES

This application claims the benefit of Egyptian Provisional application No. 25/2017 filed on Sep. 14, 2017 and Egyptian Patent Application No. 448/2018 on Mar. 13, 2018

THE TECHNICAL FIELD

The present invention relates to a device and a method for determining the position, the path, and the size of pedicel screws used in corrective scoliosis surgeries. The device is a patient-specific template with data about the size, path, and position of the screw.

PRIOR ART

Disadvantages of Current Technologies

The increasing use of pedicel screws in corrective scoliosis surgeries has posed a challenge to surgeons, especially those of limited experience. This kind of surgery is critical and should be conducted by professional surgeons. The major issue in corrective scoliosis surgery is determining the right position and path of the pedicel screw in the vertebra. Mislocating the pedicel screw leads to unsatisfactory results for both the surgeon and the patient. For example, if the screw gets out of its path it may cause compression of the nerves connected to the spine, difficulty of leg motion after surgery or loss of contact with the aorta artery behind the spine. According to previous studies and researches, more than 25% of pedicel screws are mislocated in corrective scoliosis surgeries.

Accordingly, there is a dire need for a new method that uses guides and patient-specific electronic templates for accurately determining the path, location, and size of the pedicel screw. The inventive method's error ratio is zero, as the template is designed to match the patient's vertebrae topology.

DETAILED DESCRIPTION OF THE INVENTION

The current invention relates to a device and method for determining the position, the path, and the size of pedicel screw used in corrective scoliosis and spinal disc herniation surgeries. The device is a patient-specific template used for single patient only with data about the size, path and position of the screw. The template is designed according to anatomical indicators and markers of the spinal vertebrae. The template includes two hollow cylinders with flanks for vertebrae matching and template fixation. It also contains a central hollow sphere that matches the topology of the spinous process of the vertebrae on which the template would be fixed. The said sphere is connected to the cylinders by two nerves (FIGS. 1, 2, 3, 4 & 6).

The electronic template is manufactured according to a pre-operative planning using a special software program.

The surgery is planned according to the program's data input. The patient undergoes a computed tomography scan (CT scan) that is converted to three-dimensional scan of the patient's spine. Each vertebra appears independent from the other, hence ensuring accurate surgery planning and correct determination of the position and path of the pedicel screw for each vertebra.

Pre-surgery planning is made depending on the anatomic form of the vertebra, putting into consideration the shape of the spinous process, the internal plate and the transverse process as anatomic indicators for the fixation of the electronic template on the vertebra. In the planning process, the degree of the spine curvature is determined as well as the position of each vertebra, its degree of rotation and inclination relative to the vertebral column axis. In this way, the position, the path, the inclination angle and all data related to the pedicel screw are determined. The position of the electronic template on the vertebra is determined by the aid of this data as well as surface topologies of the spinous process, the transverse process and the plate that are moved to the outer surface of the hollow cylinders and the flanks at the cylinders' ends (see FIGS. 4, 5, 6 & 7).

The said electronic templates are fixed on the vertebra depending on its outer surface's topology, according to which the template's internal surface is formed at the end of the hollow cylinders and their flanks. Hence, the template is only fitted into one location on the vertebra's surface during the pre-planned surgery. This makes it easier for surgeons, especially of limited experience, to accurately determine the position, the path and the size of the pedicel screw to be fixed on the vertebra. It is impossible for the template to be mislocated. It cannot be displaced since its unique design makes the surface of the hollow cylinder end identical to the vertebra's surface on which it is to be fixed (see FIGS. 5 & 7).

The template's design is based on the use of two hollow cylinders (FIG. 1) through which the wire or surgical drill passes forming the void space of the pedicel screw in the vertebra. There is an interfacial angle between the cylinders that varies according to the interfacial angle between the specific paths of the concerned pedicel screws (see FIG. 8). In detail, each vertebra has its own template that contains two hollow cylinders of fixed diameter. Each cylinder has a central sphere with a fixed diameter, and ends with two flanks. As illustrated in FIG. 5, each flank is adapted to match the shape of another corresponding surface of the vertebra so as to establish continuous contact therewith in a space between the outwardly projecting flank and the hollow tube. The interfacial angle between the cylinders differs from one template to another according to the vertebra's number that indicates its location, whether it is lumbar vertebra or thoracic vertebra (FIG. 9), and according to the path inclination of the pedicel screw as a main component of the invention (see FIG. 5).

As previously mentioned, the topology of the cylinders' ends (the surface that contacts the vertebra's surface) matches that of the vertebra's surface (FIG. 4). The template has a central sphere with a cavity that matches the outer surface of the spinal process for fixing the template on its pre-designed location on the vertebra only (see FIGS. 5 & 7). In other words, the surgeon cannot fix the template in a position other than that assigned during the computer-assisted surgical planning (see FIGS. 5 & 7). As illustrated in FIGS. 1, 2, and 3, the sphere (2) may have a flat portion or surface, such as along the top and bottom thereof in the illustrated orientation. This flat portion may also include a label identifying the positon of the implant as corresponding to a particular vertebrae (e.g. see T-10 in FIG. 6 and note vertebrae T-10 in FIG. 9).

The template contains two flanks at the end of each cylinder whose surface matches the outer surface of the vertebral plate. They are used for keeping the template fixed to help the surgeon to determine the pedicel screw's position and path in the vertebra. The template includes two middle nerves between the central sphere and the hollow cylinders to increase the space of the template and make it tolerant to the forces exerted by surgical instruments. In this way, the template is kept safe from breakage or displacement.

The template is produced through three-dimensional printing techniques.

Figure 1:
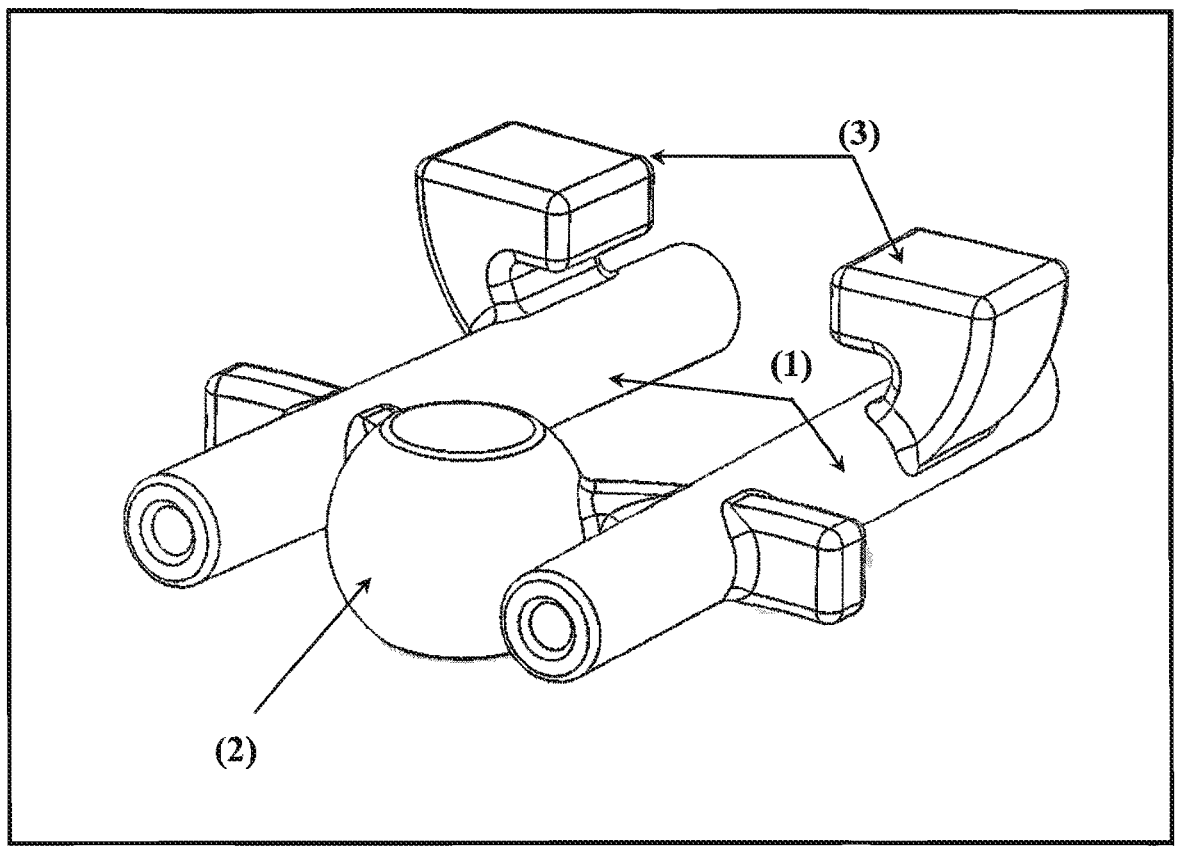
FIG. 1: represents a three-dimensional perspective for the patient-specific electronic template used for determining the position, the path, and the size of the pedicel screw. The template appears with two hollow cylinders (1), each ends with a flank (3). It also includes a central sphere at its centre (2).
Figure 2:
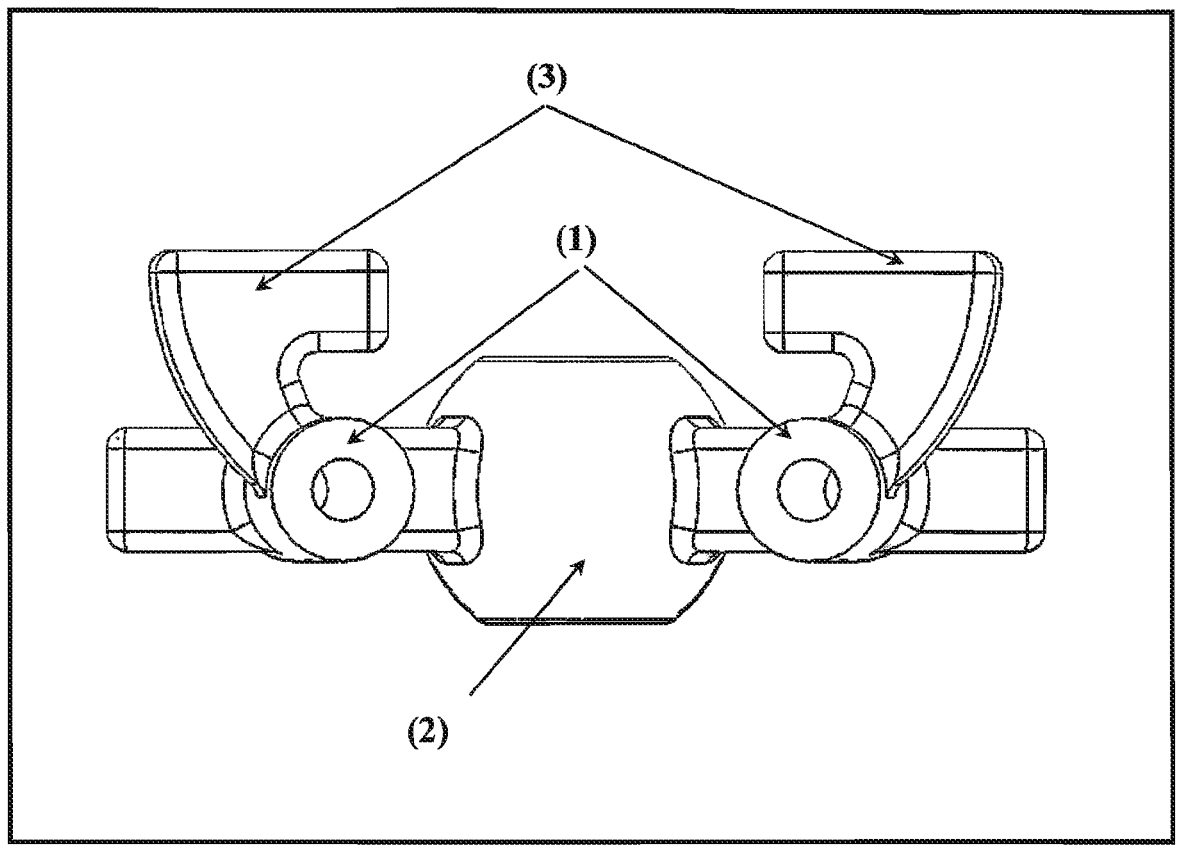
FIG. 2: represents a two-dimensional front view for the patient-specific electronic template for determining the position, the path, and the size of the pedicel screw. The template appears with two hollow cylinders (1), each ends with a flank (3). It also includes a central sphere at its centre (2).
Figure 3:
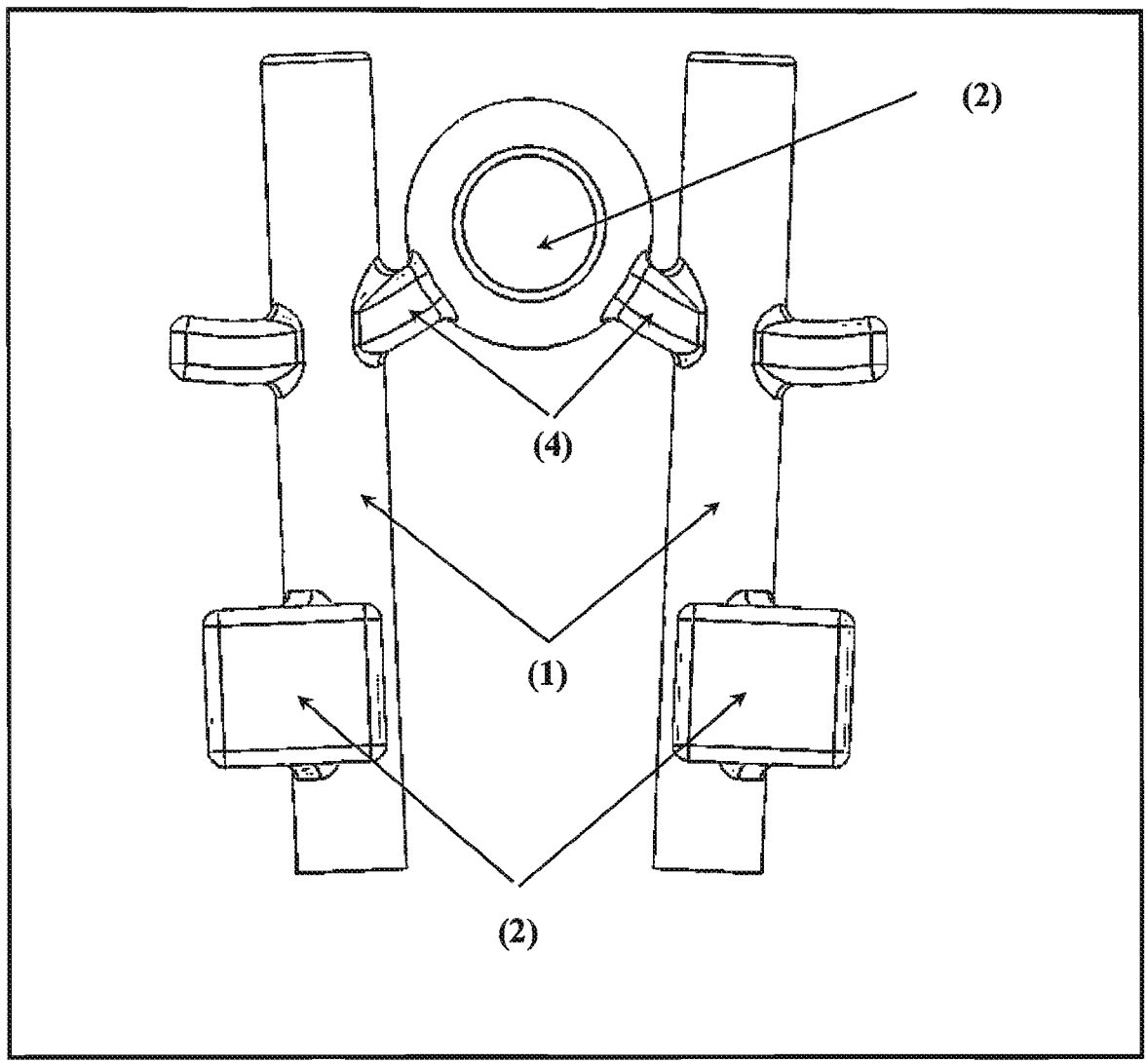
FIG. 3: represents a two-dimensional plan view for the patient-specific electronic template for determining the position, the path, and the size of the pedicel screw. The template appears with two hollow cylinders (1), each ends with a flank (3). It also includes a central sphere at its centre (2). The middle nerves appear between the central sphere and the hollow cylinders (4).
Figure 4:
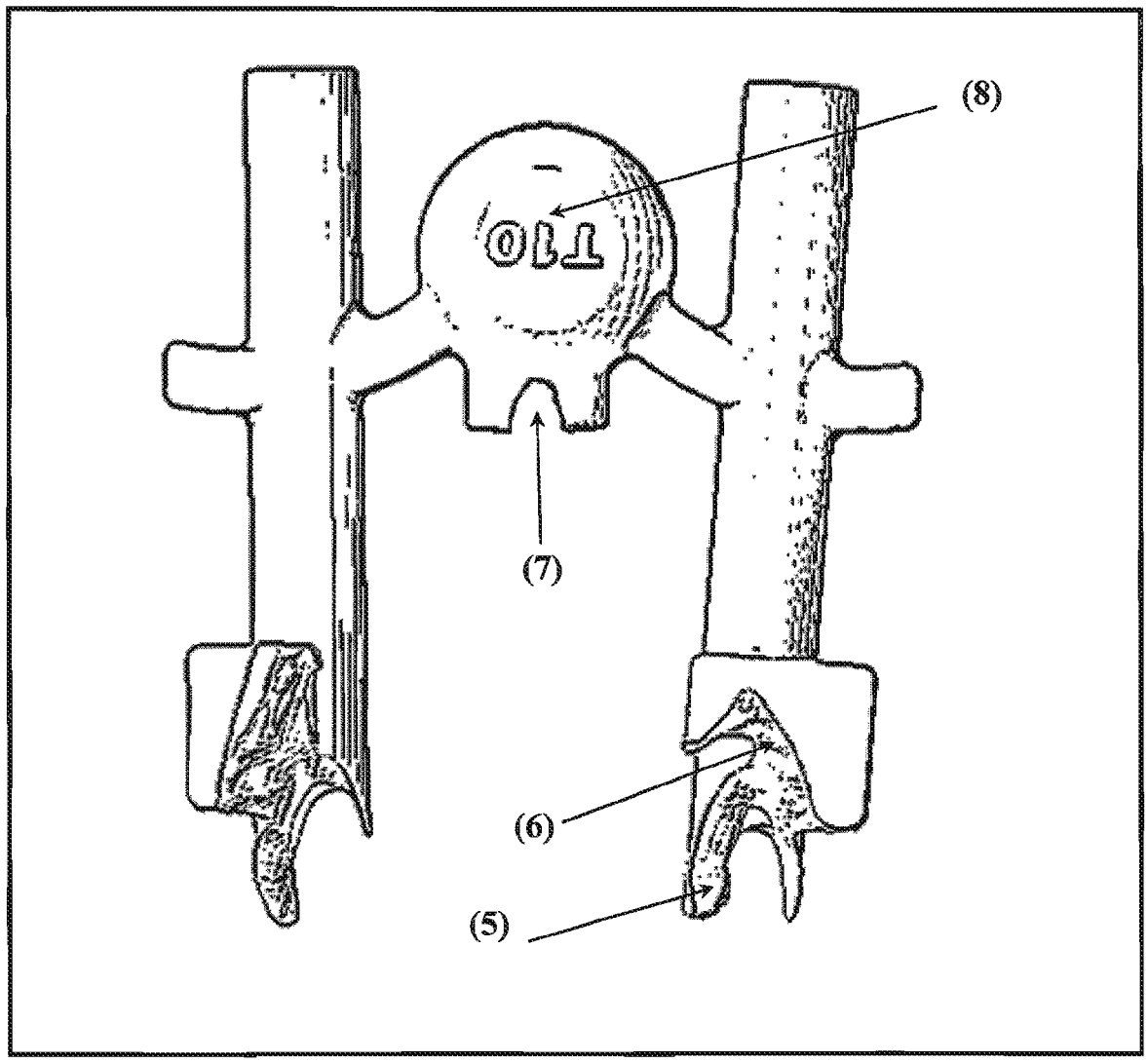
FIG. 4: represents a two-dimensional plan view for the patient-specific electronic template for determining position, the path, and the size of pedicel screw after the planning process. The end of the hollow cylinders' surface (5) appears with a topology that matches that of the plate surface and the transverse process of the targeted vertebra. The flanks at the end of each cylinder (6) have the same topology. The central sphere has a cavity that fits the outer surface of the spinal process (7). The number of the vertebra to be provided with the template is registered on the flanks to avoid confusion during surgery (8).
Figure 5:
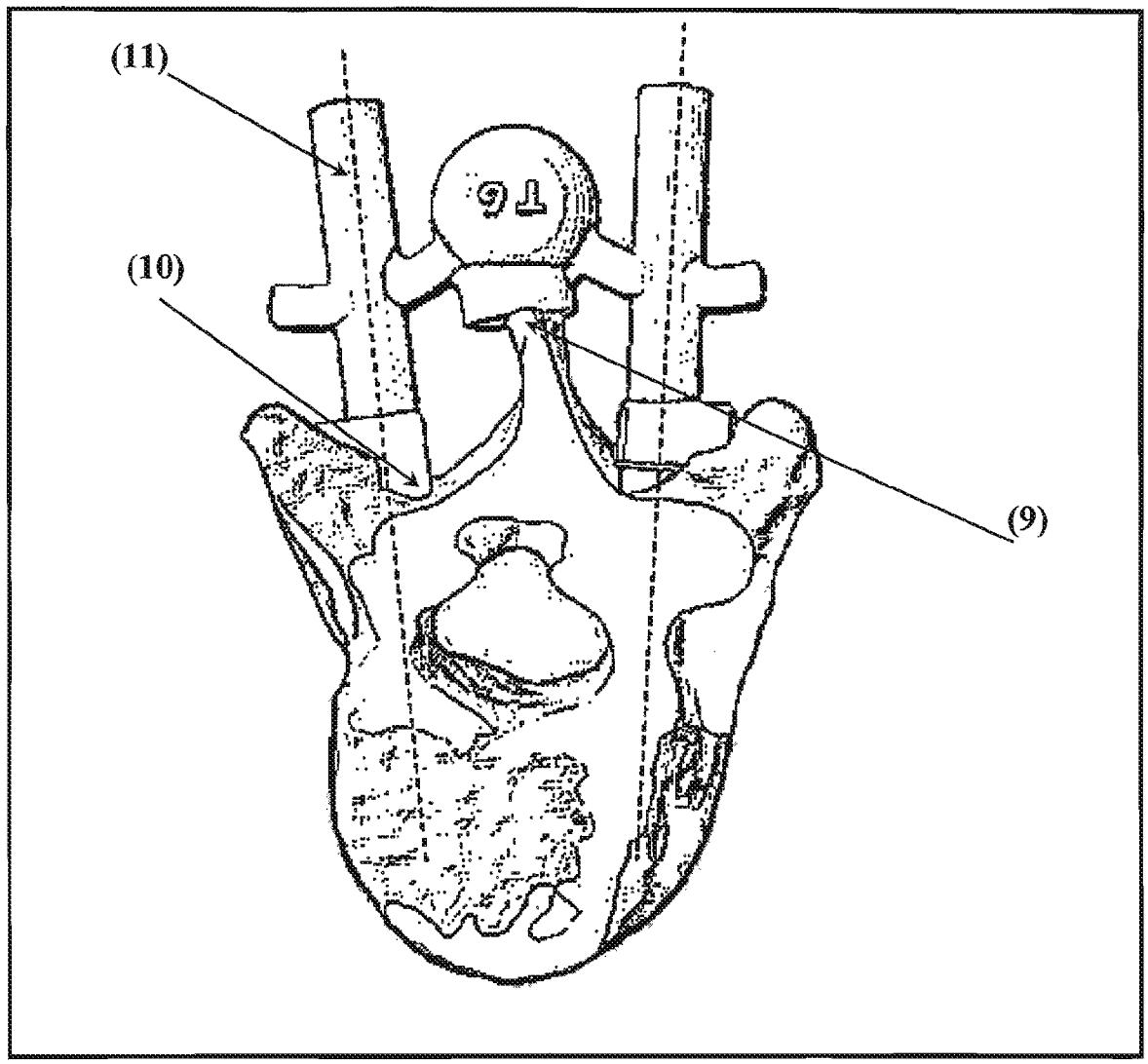
FIG. 5: represents a two-dimensional plan view for the patient-specific electronic template for determining the position, the path, and the size of pedicel screw fixed on the targeted template. The figure illustrates the location of the cylinders' ends, the plate's flanks, the transverse process (10), and the location of the centre sphere's cavity on the spinal process (9). A phantom axis for the pedicel screw path inside the template and the vertebra (11) appears in the figure.
Figure 6:
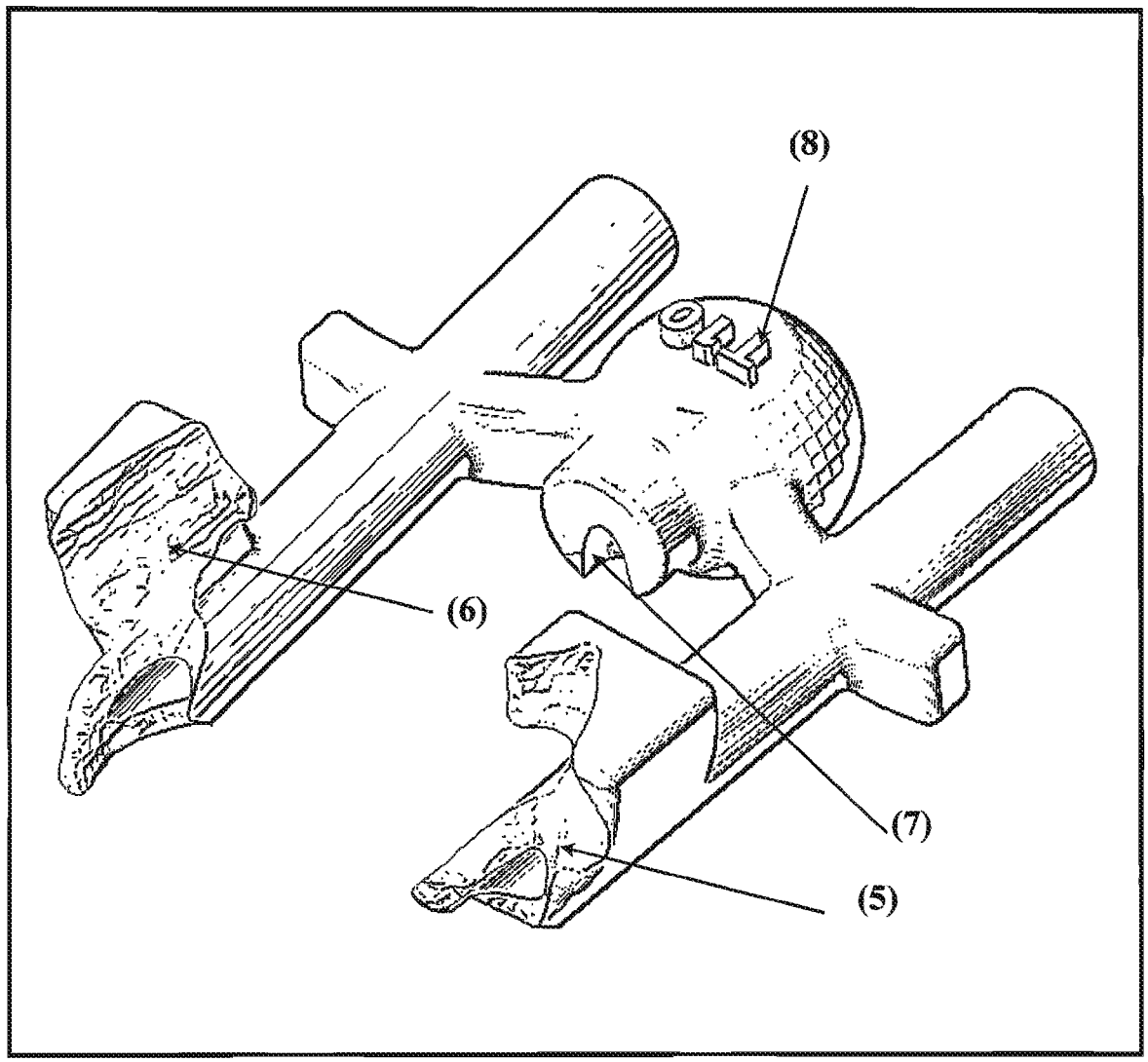
FIG. 6: represents a three dimensional perspective for the patient-specific electronic template for determining the position, the path, and the size of pedicel screw after the planning process. The end of the hollow cylinders' surface (5) appears with a topology that matches that of the plate surface and the transverse process of the targeted vertebra. The flanks at the end of each cylinder (6) have the same topology. The central sphere has a cavity that fits the outer surface of the spinal process (7). The number of the vertebra to be provided with the template is registered on the flanks to avoid confusion during surgery (8).
Figure 7:
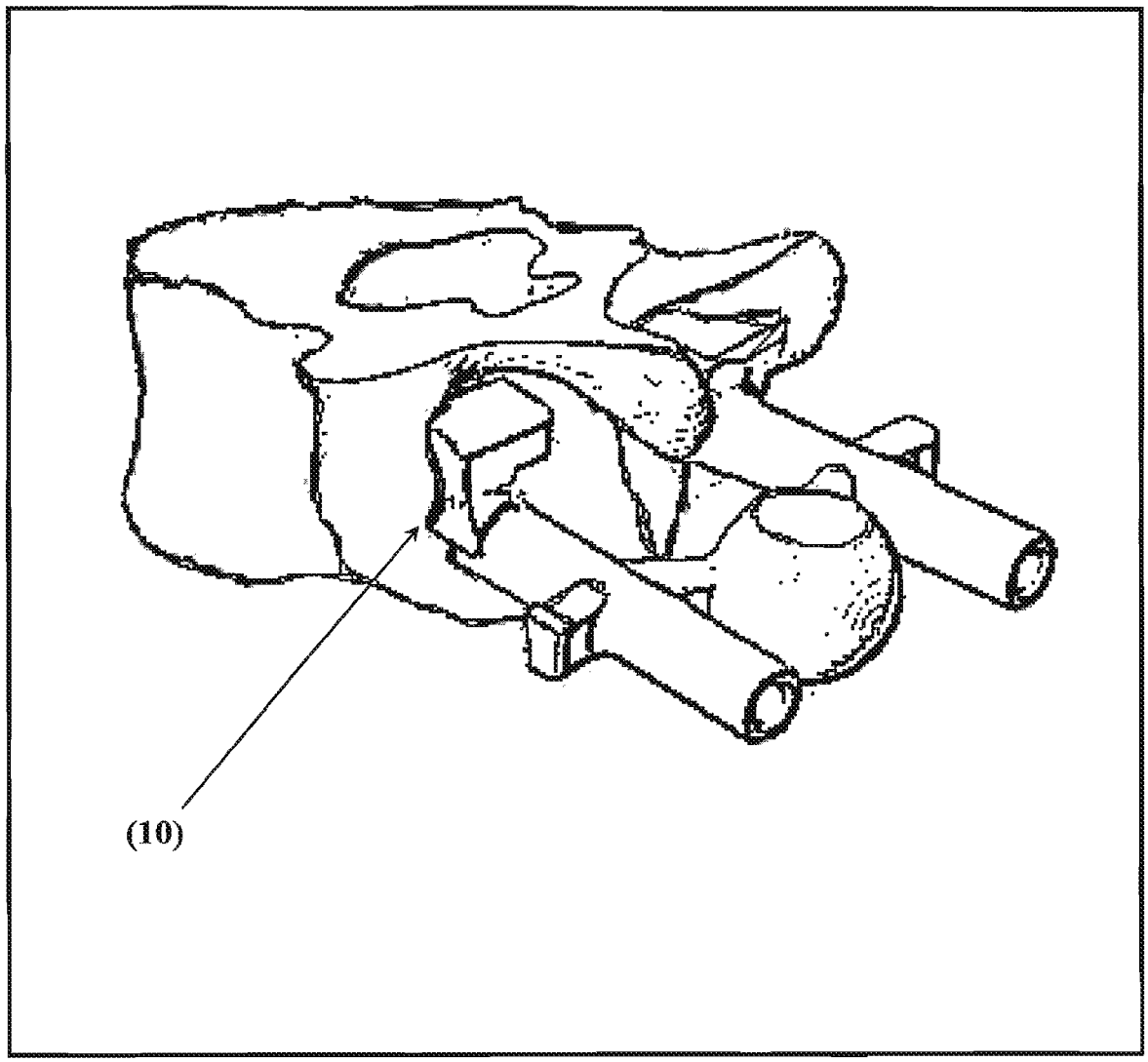
FIG. 7: represents a three dimensional perspective for the patient-specific electronic template for determining the position, the path, and the size of pedicel screw to be fixed on the targeted vertebra. The figure illustrates the location of the cylinders' ends, the plate's flanks and the transverse process (10).
Figure 8:
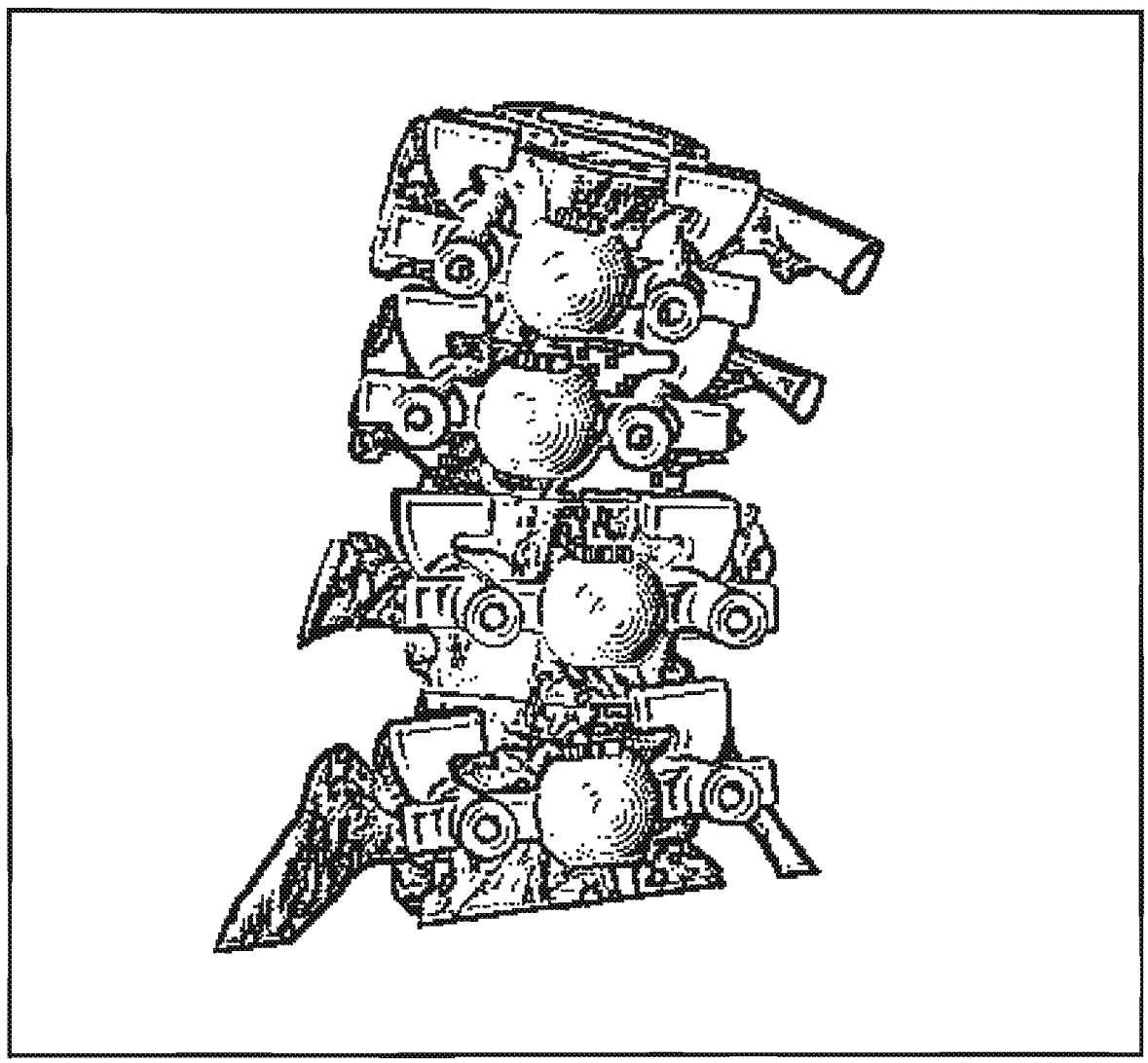
FIG. 8: represents a two-dimensional front view for a number of electronic templates fixed on their proper positions on the targeted vertebra.
Figure 9:
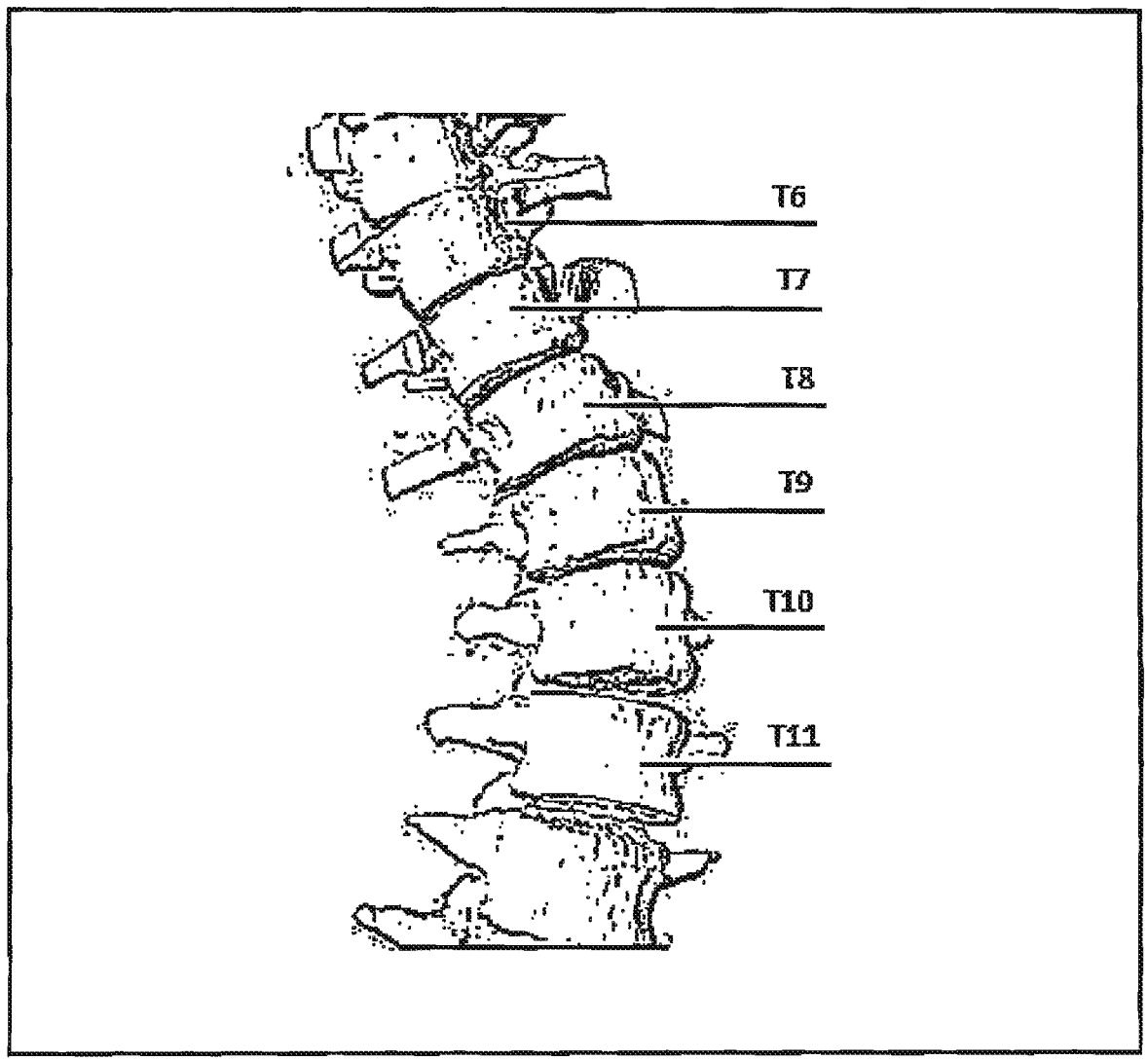
FIG. 9: represents a front view of the spine in which some vertebrae appear with conventional numbers that is registered on the template for avoiding confusion during surgery.

The invention claimed is:

1. An apparatus for determining a path, location and size of pedicle screws for installation in a vertebra of a patient undergoing corrective scoliosis or spinal disc herniation surgery, comprising:
   a pair of hollow tubes for receiving the pedicle screws, a distal end of each hollow tube adapted to contact and match a corresponding surface of the vertebra; and
   a central body located between and interconnecting the pair of hollow tubes, the central body adapted to receive a portion of the vertebra;
   wherein the central body includes a spherical outer surface, a flat portion and a cavity adapted to receive a spinal process of the vertebra.

2. The apparatus of claim 1, wherein the central body includes opposed planar surfaces.

3. The apparatus of claim 1, wherein each hollow tube of the pair of hollow tubes includes a passage with a circular shape in cross-section.

4. The apparatus of claim 3, wherein the hollow tubes form paths for delivering each pedicle screw, which paths have axes that are not parallel to each other.

5. The apparatus of claim 1, wherein each hollow tube of the pair of hollow tubes includes a flank adapted to match the shape of another corresponding surface of the vertebra.

6. The apparatus of claim 5, wherein each flank has a flat surface in a first plane parallel to a plane aligned with an axis of each hollow tube.

7. A method of manufacturing the apparatus of claim 5, comprising:
   performing a computed tomography scan on the patient to create a three-dimensional scan of the patient's spine; and
   forming the hollow tubes and flanks according to the three-dimensional scan so as to match the corresponding surfaces of the vertebra.

8. An apparatus for determining a path, location and size of pedicle screws for installation in a vertebra of a patient undergoing corrective scoliosis or spinal disc herniation surgery, comprising:
   a pair of hollow cylinders for receiving the pedicle screws, an end of each hollow cylinder adapted to contact and match a corresponding surface of the vertebra; and
   a central spherical body located between and interconnecting the pair of hollow cylinders, the central spherical body adapted to receive a portion of the vertebra and including a flat portion.

9. The apparatus of claim 8, wherein the central spherical body comprises a cavity adapted to receive a spinal process of the vertebra.

10. The apparatus of claim 8, wherein the central spherical body includes opposed planar surfaces.

11. The apparatus of claim 8, wherein each hollow cylinder of the pair of hollow cylinders includes a passage having a circular shape in cross-section.

12. The apparatus of claim 8, wherein the hollow cylinders form paths for delivering each pedicle screw, which paths have axes that are not parallel to each other.

13. The apparatus of claim 8, wherein each hollow cylinder is provided with a flank adapted to match the shape of another corresponding surface of the vertebra.

14. The apparatus of claim 13, wherein each flank has a flat surface in a first plane parallel to a plane aligned with an axis of each hollow cylinder.

15. A method of manufacturing the apparatus of claim 14, comprising:
   performing a computed tomography scan on the patient to create a three-dimensional scan of the patient's spine; and
   forming the hollow cylinders and flanks according to the three-dimensional scan so as to match the corresponding surfaces of the vertebra.

16. An apparatus for determining a path, location and size of pedicle screws for installation in a vertebra of a patient undergoing corrective scoliosis or spinal disc herniation surgery, comprising:
   a pair of hollow tubes for receiving the pedicle screws, an end of each hollow tube adapted to contact and match a corresponding surface of the vertebra, each hollow tube of the pair of hollow tubes including an outwardly projecting flank adapted to match the shape of another corresponding surface of the vertebra so as to establish continuous contact therewith in a space between the outwardly projecting flank and the hollow tube; and
   a connector connecting the pair of hollow tubes.

17. The apparatus of claim 16, wherein the connector comprises a body having a spherical portion, the body adapted for receiving a part of the vertebra.

18. The apparatus of claim 16, wherein each outwardly projecting flank presents a first topology, and the ends of the pair of hollow tubes each include a second topology matching the first topology.

19. A method of manufacturing the apparatus of claim 16, comprising:
   performing a computed tomography scan on the patient to create a three-dimensional scan of the patient's spine; and
   forming the hollow tubes and flanks according to the three-dimensional scan so as to match the corresponding surfaces of the vertebra.

20. An apparatus for determining a path, location and size of pedicle screws for installation in a vertebra of a patient undergoing corrective scoliosis or spinal disc herniation surgery, comprising:
   a pair of hollow tubes for receiving the pedicle screws, a distal end of each hollow tube adapted to contact and match a corresponding surface of the vertebra; and
   a connector connecting the pair of hollow tubes, the connector including a cavity adapted to receive a spinal process of the vertebra, the connector further including a spherical outer surface and a flat portion including a label corresponding to the vertebra;
   wherein each tube includes a proximal end adapted for receiving one of the pedicle screws, and the connector is located distally of the proximal ends of the hollow tubes.

* * * * *